United States Patent
Biglieri et al.

(10) Patent No.: US 7,023,211 B2
(45) Date of Patent: Apr. 4, 2006

(54) NUCLEAR MAGNETIC RESONANCE IMAGING APPARATUS

(75) Inventors: Eugenio Biglieri, Masio (IT); Osvaldo Pugliese, Genoa (IT)

(73) Assignee: Esaote, S.p.A., Casale Monferrato (IT)

( * ) Notice: Subject to any disclaimer, the term of this patent is extended or adjusted under 35 U.S.C. 154(b) by 0 days.

(21) Appl. No.: 10/786,300

(22) Filed: Feb. 26, 2004

(65) Prior Publication Data
US 2004/0189301 A1    Sep. 30, 2004

Related U.S. Application Data

(62) Division of application No. 10/154,909, filed on May 28, 2002, now Pat. No. 6,720,770.

(30) Foreign Application Priority Data
May 28, 2001 (IT) .......................... SV2001A0017

(51) Int. Cl.
*G01V 3/00* (2006.01)
(52) U.S. Cl. ...................... 324/322; 702/224
(58) Field of Classification Search ................ 324/318, 324/322, 307, 309, 306, 300; 702/224, 200
See application file for complete search history.

(56) References Cited
U.S. PATENT DOCUMENTS

| 4,885,538 A | 12/1989 | Hoenniger, III et al. |
| 5,175,710 A | 12/1992 | Hutson |
| 5,245,587 A | 9/1993 | Hutson |
| 5,348,020 A | 9/1994 | Hutson |
| 5,490,516 A | 2/1996 | Hutson |
| 5,662,109 A | 9/1997 | Hutson |
| 6,339,717 B1 | 1/2002 | Baumgartl et al. |

(Continued)

FOREIGN PATENT DOCUMENTS

EP    1 004 269 A1    5/2000

(Continued)

*Primary Examiner*—Louis M. Arana
(74) *Attorney, Agent, or Firm*—Buchanan Ingersoll PC

(57) ABSTRACT

Nuclear Magnetic Resonance imaging apparatus, comprising a unit (1) for exciting and receiving nuclear spin signals, an electronic driver unit (3) for driving the devices of the signal exciting and receiving unit, an electronic unit for controlling the electronic driver units, a unit (6) for processing the received signals, a unit (5) for displaying the image data processed, a unit (6) for filing and storing the image data, a unit (4) for entering commands, the said units being formed partially by specific hardware and partially by a commercial available personal computer running specific programs, a bidirectional communication bus (7') being further provided for the communication between the different units, which bus encodes data consistently with the communication buses normally used to interface computer peripheral devices, and/or in communication networks, or the like, characterized in that at least one part of the personal computer hardware is formed by a client computer (30) and part by a server computer (Server PC) communicating one with the other by means of a conventional network (7).

5 Claims, 3 Drawing Sheets

U.S. PATENT DOCUMENTS

| | | |
|---|---|---|
| 6,346,814 B1 | 2/2002 | Carrozzi et al. |
| 6,348,793 B1 | 2/2002 | Balloni et al. |
| 6,362,620 B1 | 3/2002 | Debbins et al. |
| 6,366,094 B1 | 4/2002 | Vassallo et al. |
| 6,377,830 B1 | 4/2002 | Carrozzi et al. |
| 6,430,428 B1 | 8/2002 | Lindstedt |
| 6,492,812 B1 * | 12/2002 | Debbins et al. ............. 324/309 |
| 6,598,011 B1 * | 7/2003 | Koritzinsky et al. ........ 702/185 |
| 6,608,628 B1 * | 8/2003 | Ross et al. .................. 345/619 |
| 6,675,210 B1 * | 1/2004 | Takeo et al. ................ 709/224 |

FOREIGN PATENT DOCUMENTS

| | | |
|---|---|---|
| EP | 1 262 786 A3 | 12/2002 |
| JP | 09-319516 | 12/1997 |
| WO | 96/32065 | 10/1996 |

* cited by examiner

NUCLEAR MAGNETIC RESONANCE IMAGING APPARATUS

This application is a divisional of application Ser. No. 10/154,909, filed on May 28, 2002 now U.S. Pat. No. 6,720,770 which claims priority under 35 U.S.C. §§ 119 and/or 365 to IT SV2001A00017 filed in Italy on May 28, 2001; the entire contents of which are hereby incorporated by reference.

BACKGROUND OF THE INVENTION

1. Field of the Invention

The invention relates to a Nuclear Magnetic Resonance imaging apparatus.

2. Discussion of Related Art

In document U.S. Pat. No. B1-6,339,717 a medical examination system, particularly a magnetic resonance imaging apparatus is disclosed showing the above described architecture. The apparatus has a host computer unit, a control computer unit and an image computer unit. The three computer units are integrated in a commercially obtainable personal computer that contains at least two of the said computers, preferably all three of the said computers. The integrated hardware architecture is further operated also by a commercially available operating system such as Windows® or other kinds of operating systems. Part of the hardware and specifically, the units for driving the apparatuses specific exciting and receiving units as well as the analog to digital and digital to analog converters for transforming the digital control signals in analog signals for controlling the driving units and for transforming the analog received data in digital data, are housed within the frame of the nuclear magnetic resonance apparatuses, while the conventional personal computer hardware is housed in a separated case or console. Thus U.S. Pat. No. B1-6,339,717 teaches to separate the said personal computer hardware from the nuclear magnetic resonance excitation and receipt unit.

Although the use of commercial hardware in the form of personal computer already contributes to lower costs of the apparatuses, a considerable amount of hardware is reproduced in each machine. The computational power of each such personal computer hardware is not completely exploited by carrying out the control and processing functions of only one machine.

Furthermore, a particular kind of medical examining apparatuses, particularly of magnetic resonance imaging apparatuses, is getting more and more interesting for the user, due to its lower costs, to the reduced dimensions and to the more simple way to install it. Such apparatuses are the so called "Dedicated MRI" apparatuses which have magnetic structures which are relatively small and which are constructed for examination of only special anatomical districts of the entire body, such as the foot, the knee, the elbow, the head, the shoulder, the hand, etc.

Thus in a bigger medical cabinet or in a diagnostic department many of these specific apparatuses may be provided each one having its own hardware.

OBJECTS AND SUMMARY

It is important in this case to reduce so far as possible costs and volume of the apparatuses.

It is an object of the present invention to provide for a medical examining apparatus, particularly for a magnetic resonance imaging apparatus, which construction helps in reducing the overall dimensions of the apparatus or the need of installation space for the apparatus and in reducing costs.

Furthermore it is another object of the present invention to provide a medical examination apparatus, particularly a magnetic resonance imaging apparatus, having an hardware architecture which facilitates the configuration and upgrade of the apparatus by limiting as far as possible the amount of hardware which needs to be substituted for configuration and upgrade.

The invention achieves the above mentioned aims by means of a nuclear resonance imaging apparatus, in which at least one part of the personal computer hardware is formed by a client and a server computer communicating one with the other by means of a conventional network protocols.

Many different configurations of the client-server architecture are possible which has different levels of advantage.

In one possible configuration, the client computer is mainly formed by a motherboard comprising a local CPU and only a network interface such as a conventional network card or network controller and the local client computer, this means the client computer associated to the exciting and receiving units of the magnetic resonance imaging apparatuses, only manages the communication with the server computer in which one all the hardware units and software reside which are necessary for controlling the driving units of the exciting and receiving units located in the machine frame of the exciting and receiving units themselves, for processing the received data obtaining from them the image data, for displaying, filing, storing the said image data, and for receiving and processing the commands inputted by the machine operators and also for managing the network communication.

Since network protocols allow a wide sharing of peripherals directly connected with the client and or the serve computer, some of the peripherals may be connected directly only to the client computer or to the hardware computer.

Other peripherals may be connected or interfaced directly with both computers depending on the level of hardware doubling requested by the operators for facilitating their job.

In any case, transferring most of the controlling and processing tasks to a server computer allows to reduce the hardware needed for configuring the client computer which must in this case carry out local minor or limited tasks.

For example, the display monitor or input devices must be provided for the client computer and for the server computer. This hardware doubling might be also chosen for other peripherals such as mass storage devices and/or portable data devices writer or readers such as floppy disk drivers, CD-rom or CD-writable or rewritable, DVD-ROM or DVD writable or rewritable drivers or other kind of storage device readers and writers such as compact flash, PCMCIA memory stick readers and writers, or the like.

The client computer may have also a hard disk unit or other kind of memory unit for storing the communication protocols and control software and the operating system as well as the software for carrying out limited local tasks.

It is to be appreciated that the client computer in any case needs a reduced computational power, limited hard disk or memory for the local software and a reduced RAM as the server computer. Thus also if many of the peripherals is provided in the configuration of the client local computer as well as in the configuration of the server computer costs of the client computer will be considerably lower than the costs of the server computer.

It is also to be considered that in case of use of only one apparatus, the client computer might be very simply configured as the server computer so that no client computer will be necessary since more than one apparatuses is provided.

In case of use of two or more apparatuses, the client server architecture however allows to reduce costs for hardware, and software because the second apparatus will need only to be equipped with the client computer, while it will be put in communication with the server computer of the first apparatus.

Thus a second, a third and further apparatuses may be added very simply to the network by simply providing the server computer with a switch or a hub having the requested number of ports which are needed.

Each one of the apparatuses connected to the server may be differently configured relating to their client computer and the different peripherals of the different client computer configurations may be or not shared by each or part of the apparatuses connected to the network.

Relating to the above mentioned possibility it is to be noticed that the above described client/server architecture may be in any case also used in any kind of medical examination device. So also examination devices of different kind such as ultrasound, radiographic or similar apparatuses may be connected to the network, thereby sparing resources also for this kind of apparatuses. In this case the server computer must be provided also with the controlling, processing and displaying programs for each different kind of apparatus connected to the net.

It is always possible to decide how far controlling, processing and displaying or storing tasks of the apparatuses connected to the network has to be integrated in the server computer.

Furthermore the client/server architecture allows to differentiate different diagnostic divisions by defining the common server of the apparatuses of one division as local server and by connecting this server to a further net controlled by a central server or framework computer which then collects information from the different local servers. This allows better cooperation of the different diagnostic divisions relating to identifying and collecting information of a patient and also easier upgrades of the apparatuses of the different divisions which may be carried out centrally, for example when a software upgrade or other similar jobs have to be carried out.

It is also to be stressed out that the client computer needing a reduced hardware amount will show also smaller dimensions and that it might be integrated very simply in the frame or case supporting the exciting and receiving units or in devices associated therewith such as in the frame of an examination table or chair, or the like.

Also the apparatus dedicated monitor and/or input device and/or storing device might be provided in a very small console which might be associated very easily to the frame of the exciting and receiving unit or to the examination chair or table.

The above architecture allow simply to use the same host computer combined with the specific programs to control more than one imaging apparatus.

The client computer associated to the apparatuses resident exciting and receiving units as well as to the apparatuses resident specific hardware units for driving the said exciting and receiving unit may be configured in different manners so to provide integration with more peripherals which might be chosen to be added to the MRI apparatus, such as a video cards for driving a local monitor and/or interfaces for driving mass storage devices as floppy disk drivers, CD_ROM or CD writable or rewritable drivers or the like.

The host computer might be configured as a server having a switch or hub for connecting more than only one apparatus and might be provided with the image reconstruction software, with the software for controlling the driver units of signal excitation and receiving units according to different kinds of imaging methods known.

The host computer might be itself a regional server which is a client of a central server of a server controlling a network formed by more than one regional server each one controlling one or more than one MRI apparatuses.

The above mentioned architecture also allows to use the same regional server to control different kinds of imaging apparatuses having also a client computer as local control unit, such as for example X-ray imaging apparatuses, ultrasound imaging apparatuses etc.

According to a further improvement of the hardware architecture of the present invention, there is provided a communication bus which is a backbone of the driving unit or units of the excitation and receiving unit or units and of the associated local computer and each driving unit and each unit of the client computer is made in the form of one or more electronic cards each one having an input/output interface with the communication bus, while the input data and output data exchanged between the single electronic cards is coded according to a common data coding protocols.

By providing each unit and/or each electronic card forming a unit with its communication interface for the specific communication bus in use, the single units of the apparatus may be added or removed very easily.

Therefore, the apparatuses may be configured in a very easy and inexpensive manner, not only relatively to the components of the client computer and to its interface with the driving units of the exciting and receiving units but also relatively to each of the said driving units which has to be specifically designed and constructed for the specific exciting and receiving units. Thus thanks to the above mentioned architecture it is possible to remove, add and substitute electronic cards for upgrading, integrating or repair purposes. It is also possible to define a basic hardware configuration which is required for the proper operation of the apparatus relating to its basic functions by leaving open the possibility to upgrade the configuration of the apparatus at any time when needed with additional units or cards for executing further functions.

It is also possible to simply upgrade older dedicated hardware, such as the magnetic coils feeding units and/or the driving units of the receiving coils and/or further hardware needed for driving temperature probes or further control and survey functions by simply removing the older electronic cards and substituting them with the newer ones.

Such open architecture of the specific hardware for driving the exciting and receiving units and the client computer hardware has further advantages since it gives a better possibility to carry out diagnostic hardware tests through the server computer or by means of diagnostic systems which may be interfaced with the communication bus for collecting and analyzing the hardware. The diagnostic procedures allow to univocally address each electronic card, since the communication bus requests for each card connected therewith to have a precise and univocally recognizable address.

More in detail the in their basic configuration the driving units of the exciting and receiving units may include, a central image data supervision, pre-processing and reconstruction unit, which controls a control and capture unit as well as a thermal and magnetic control unit, and a receiver unit.

All these sub-units of the driving unit are provided with communication devices and are connected to one other and to the client computer and its peripherals and through the said client computer to the server computer and its peripherals by using the same bus or the same communication lines.

As a further improvement, the use of a console consisting of a client computer and a server computer formed by a conventional personal computer with appropriate functions, allows to use peripheral devices for command entry, display, print, storage and communication with conventional networks, such as keyboards, monitors, modems, or network adapters, printers, etc.

Furthermore, it is also advantageously possible to adapt currently enhanced video-game peripherals to diagnostic use, the apparatus, or at least some functions thereof being easily controllable, for instance by a joystick or a game pad, which allows to enter commands in a more immediate and intuitive manner.

The architecture of the hardware according to the invention allows to easily implement the different operating modes of an imaging apparatus of whichever kind by simply loading the corresponding software in the server computer and/or in the client computer. The different modes within the same kind of apparatus often do not require the physical presence of dedicated electronics, the latter being replaced by control software packages. When a different examination apparatus has to be considered, than it is necessary to provide only a very limited part of the entire hardware that has to be replaced with the specific hardware designed for driving the specific examination and receiving units. Hence, for instance, a unique server console can be used both for control and image display through different apparatuses, by simply loading the software required for the specific apparatus. Moreover, any improvement, e.g. for MRI machines, the implementation of new or different imaging sequences, may be simply obtained by loading the corresponding software into the server computer memory and, if needed, by replacing and/or adding cards or parts of the electronics or sub-units of the unit for driving the signal exciting and receiving unit. The server computer will then be operated in order to communicate the new sequences to be applied in one or more or all the apparatuses connected to the server computer by means of their client computer.

The considerable advantages in terms of flexibility, easy maintenance and upgrade, cost savings and fast construction, which may be achieved by the arrangements of the present invention are apparent from the above description.

BRIEF DESCRIPTION OF THE DRAWINGS

The characteristics of the invention and the advantages derived there from will appear more clearly from the following description of a non limiting embodiment, illustrated in the annexed drawings, in which.

DETAILED DESCRIPTION OF THE PREFERRED EMBODIMENTS

Figure 1:
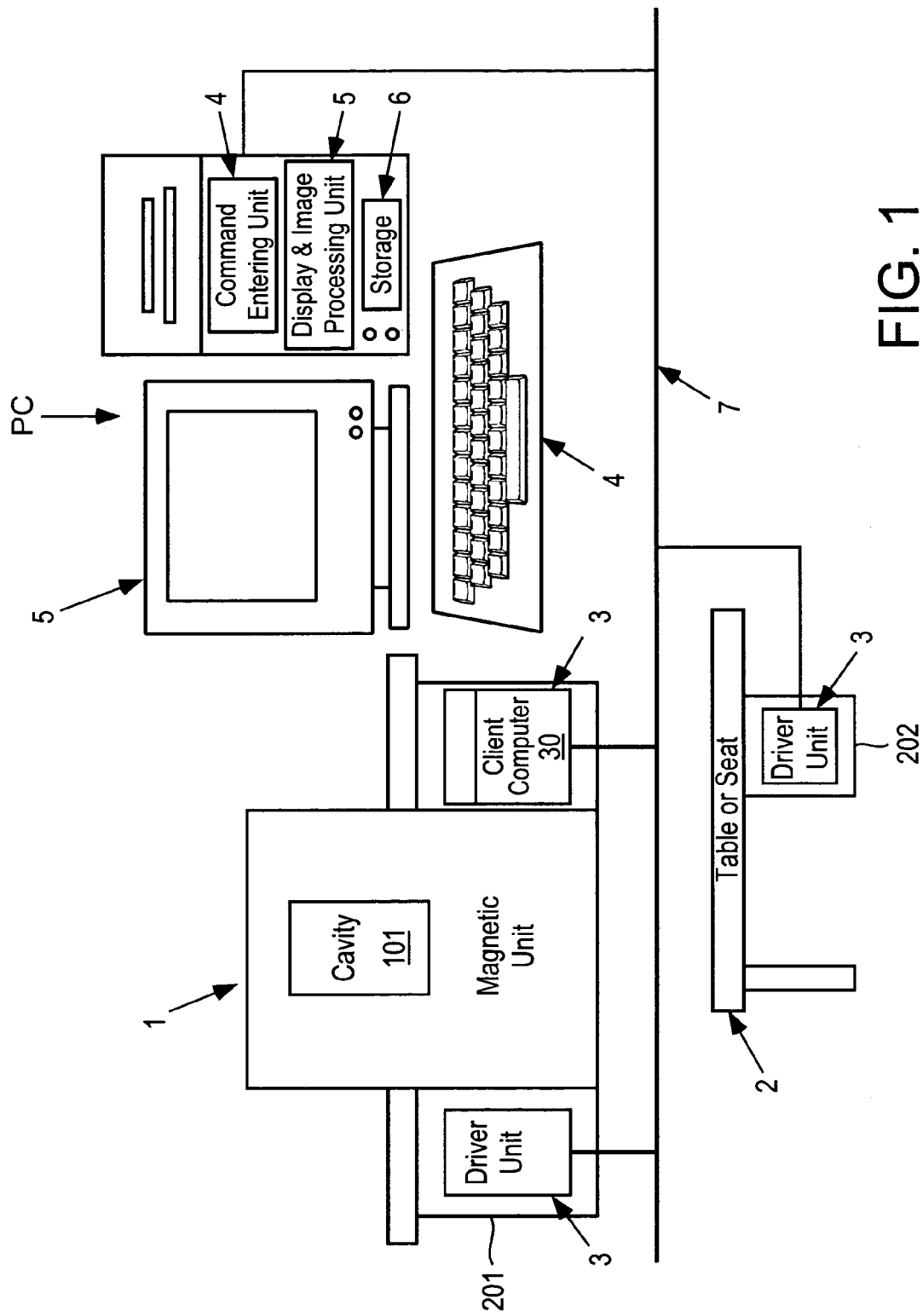
FIG. 1 is a schematic view of an embodiment of a Nuclear Magnetic Resonance imaging apparatus according to the invention.

With reference to FIG. 1, a Nuclear Magnetic Resonance imaging machine comprises a signal exciting and receiving unit consisting of a magnetic unit 1. The magnetic unit includes permanent or resistive or superconducting magnets for generating a static field inside a cavity 101 which is designed to receive the patient body or a part thereof, particularly a limited anatomic region, such as a leg, an arm, the head, etc.

As is generally known, different coils are associated to the static field generating magnet, including:

excitation coils, for exciting nuclear spins;

magnetic gradient generating coils, for selecting the section plane along which imaging has to be performed, for encoding nuclear spins to univocally identify the signals transmitted at a predetermined space position and univocally assign the received data to a predetermined pixel of a pixel matrix which forms the displayed image;

receiving coils, for receiving magnetic resonance echoes.

Also, other means are provided, such as temperature control sensors and/or means for heat increase or generation and means for heat dissipation, which are designed to set and maintain a predetermined operating temperature, etc.

All the above elements are well-known and widely used in Nuclear Magnetic Resonance imaging machines of any type and size, both for total body machines, i.e. those designed to accommodate the whole patient body or a substantial part thereof, and for dedicated machines, i.e. those adapted to only accommodate specific limbs or limited parts or regions of the patient body. The geometry of the magnetic structure, i.e. of the cavity for accommodating the body under examination or the part thereof may also be of any type, and particularly either of the open C- or U-shaped type, or consisting of two poles separated by columns, or of the annular, closed type.

The machine shown in the Figures has a closed, i.e. annular magnetic structure and the cavity is only open at the two end sides transverse to the axis, but the invention is intended not to be limited to apparatuses having only this kind of magnetic structure.

A patient table or seat, which may have any construction and is denoted with numeral 2, is generally associated to the magnetic unit. Particularly, the patient table or seat 2 may have a structure adapted to form closable housing compartments, as is schematically shown in FIG. 1.

The magnetic unit or structure, with the components listed above, is associated to control, monitoring and processing units, which have the function to control and adjust the various components of the magnetic structure and to receive and process echo signals to extract there from all data useful for the reconstruction thereof into an image formed by an array of light image dots, the so-called pixels, whose brightness and/or color are univocally related to the received data and whose position is related to the position, within the body part under examination, wherefrom the echo signal was transmitted.

Particularly, and as a rule, an electronic unit 3 for driving the signal exciting and receiving devices, a unit 4 for entering commands to the signal exciting and receiving unit, a display and image processing unit 5 and a filing and storage unit 6 are associated to the magnetic unit.

The unit 3 for driving the signal exciting and receiving devices is contained in the case of the magnetic unit 1 and/or possibly also at least partly contained within the structure of the patient table 2, in one part thereof 202, for instance a support column, having the form of an switchboard.

The units for entering commands 4 to the signal exciting and receiving units, for display and image processing 5 and for filing and storage 6 are included, partly as hardware peripherals and partly as software programs, in a traditional personal computer indicated as server PC in FIG. 1.

The communication between the unit 3, contained in the case of the magnetic unit and/or in the structure of the patient table, with the units 4, 5, 6 of the control console provided by the server personal computer is obtained by means of a communication network denoted with numeral 7. The network 7 connects the server computer with a client computer 30 which is associated to the driver units 3 and also contained in the case of the magnetic unit 1 and/or possibly also at least partly contained within the structure of the patient table 2, in one part thereof 202, for instance a support column, having the form of an switchboard.

The communication bus may be of any type, e.g. a conventional communication bus of the Ethernet type, of the SCSI or USB type or of any other type, which allows multiplex communication among several units.

Once the type of bus to be used is selected, the implementation of interfaces with the bus 7 on the individual units 3, 4, 5, 6 is well-known in the art.

Figure 2:
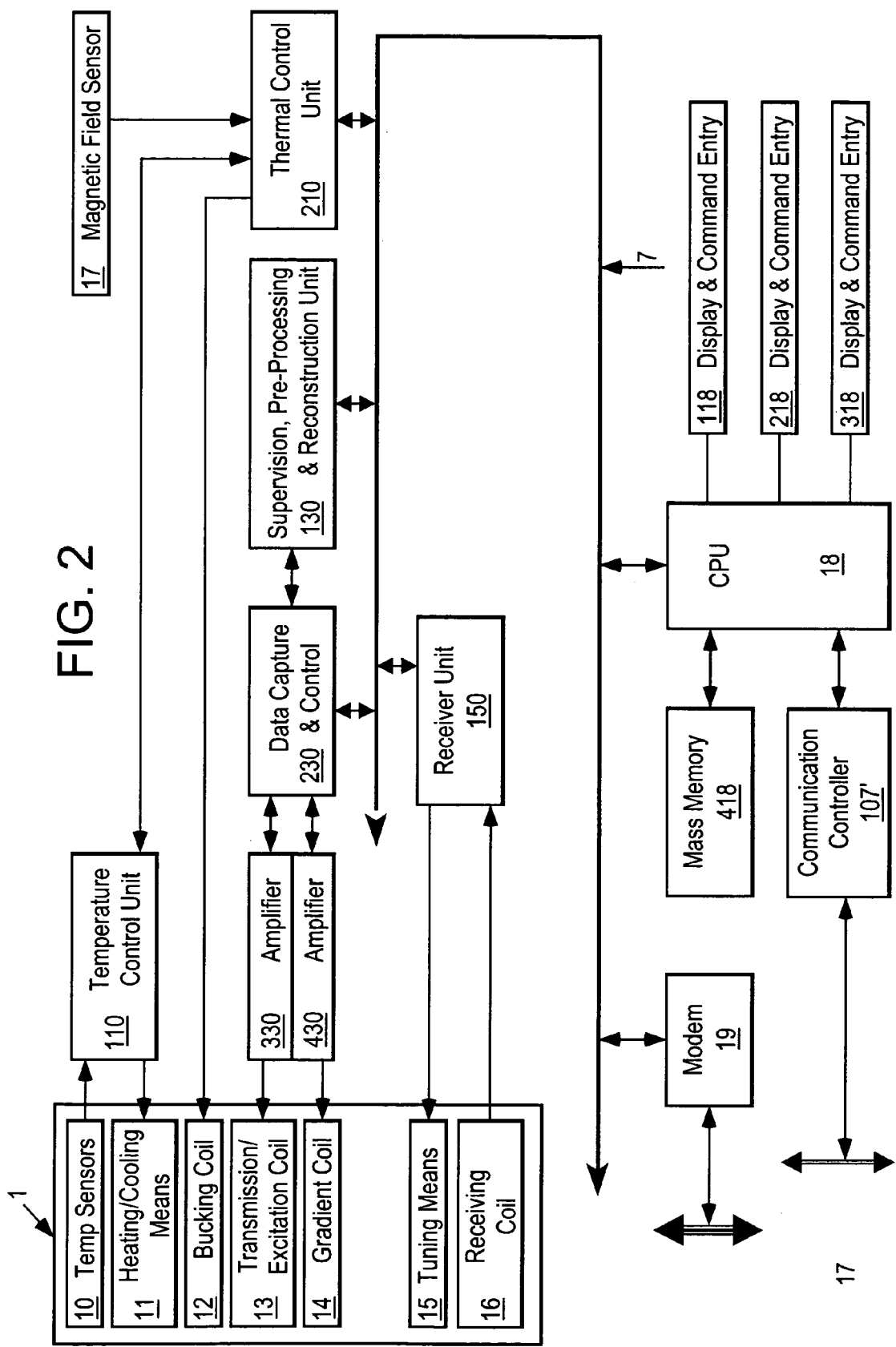
FIG. 2 shows a more detailed block diagram of the apparatus of FIG. 1.

FIG. 2 shows in greater detail what has been generally described with reference to FIG. 1.

The magnetic unit 1 includes several components, as shown in the figure, that is, in addition to static field generating magnets, temperature sensors 10, heating and/or cooling means 11, at least one bucking coil 12, at least one transmission or excitation coil 13, one or more gradient coils 14, tuning means 15 and at least one receiving coil 16, as well as one or more magnetic field sensors 17.

The temperature sensors and the heating and/or cooling means are controlled by a temperature control unit 110 which includes means for reading the signals of the sensors 10 and means for supplying the heaters and/or coolers 11, which are controlled by a thermal control unit 210 based on the actual detected temperature and on the comparison thereof with the preset nominal values.

The thermal and magnetic control unit also controls the bucking coil 13 to correct the static magnetic field with reference to the variations induced therein by external magnetic fields and based on the actual field values detected by the magnetic field sensors 17. A supervision, pre-processing and reconstruction unit 130 controls a data capture and control unit 230 which in turn controls the amplifiers 330 and 430 for the signals provided to the transmission or excitation coil 13 and to the gradient coil/s 14 respectively.

A receiver unit 150 is responsible for tuning 15 the receiving coil 16 and identifying the receiving coil 16, as well as for receiving the data collected by said receiving coil 16.

These units are all contained wholly or at least partly inside the case of the magnetic unit 1, and/or wholly or at least partly in a closable compartment of the structure of the patient table 2.

The supervision, pre-processing and reconstruction unit 130, the control and data capture unit 230, the thermal and magnetic control unit 110 and the receiver unit 150 communicate with one another and/or with other units by means of a bus 7'. In order to allow this communication each unit or electronic circuit card or board has its own Input/output on board controller which is suitable for communicating through the chosen bus 7'.

More particularly, these units communicate with the CPU 18 of a conventional personal computer, having conventional peripherals, according to the desired or required quantity and type.

The display and command entry peripherals denoted with numerals 118, 218, 318, as well as a mass memory for filing and a memory for the specific image processing and display software, collectively denoted with numeral 418 are connected to the CPU 18. The CPU 18 may also communicate by means of a network communication controller 107 such as a LAN or ETHERNET card with a local communication network 7, such as a LAN network or an Intranet or Internet network, or a network of any other suitable type. The Server Personal Computer indicated by Server PC in FIG. 1 communicates with the client computer by means of the network 7. The network 7 is also connected with a modem unit 19, which allows connection to a local network and/or to other machines connected to the local network via a telephone line. This redundancy, besides allowing to communicate with local networks in other locations, is also an alternative method for connection with the local LAN network, in case of temporary communications problems of the network interfaces.

As it is apparent from the above description, the communication network is not only provided between the client and server Personal computers but it is extended also inside the driver units 3, thereby providing the greatest configuration and operation freedom as well as allowing to add functional units with new functions and/or to replace old type units with more modern units. Replacement operations, both for upgrading and repairing purposes are apparently easy. As long as signals are encoded consistently with the bus in use, any unit may be connected to the communication bus 7' and is able to exchange data and commands with the other units.

The construction of the apparatus according to the invention also allows additional configurations, which might be highly advantageous in terms both of cost effectiveness and of organization and management. In fact, the connection of various units through a conventional data bus allows to control several apparatuses, even of different types, from a single location or from a limited number of locations.

A system may be also provided which comprises several machines organized in groups, each having a single dedicated client personal computer in the form of a conventional computer, each conventional client computer being connected to a server Personal Computer via a network. In this case, the server computer may contain many different programs for controlling image acquisition and/or processing and reconstruction procedures, e.g. a database of Nuclear Magnetic Resonance imaging sequences, a database of signal filtering and/or processing procedures aimed at modulating the definition and/or the contrast and/or the signal-to-noise ratio and/or the imaging times, whereas the client computers may access the server databases to extract programs and/or image acquisition and/or processing procedures from said databases.

By this arrangement, client computers may be configured in a more inexpensive manner, especially as regards memories and graphic sections. Also, limited-quality means, e.g. monitors or printers, may be provided locally, while higher-quality means are associated to the server. This provides considerable resource savings, and allows, for instance to purchase higher-quality monitors and/or other display means, such as printers or the like.

Figure 3:
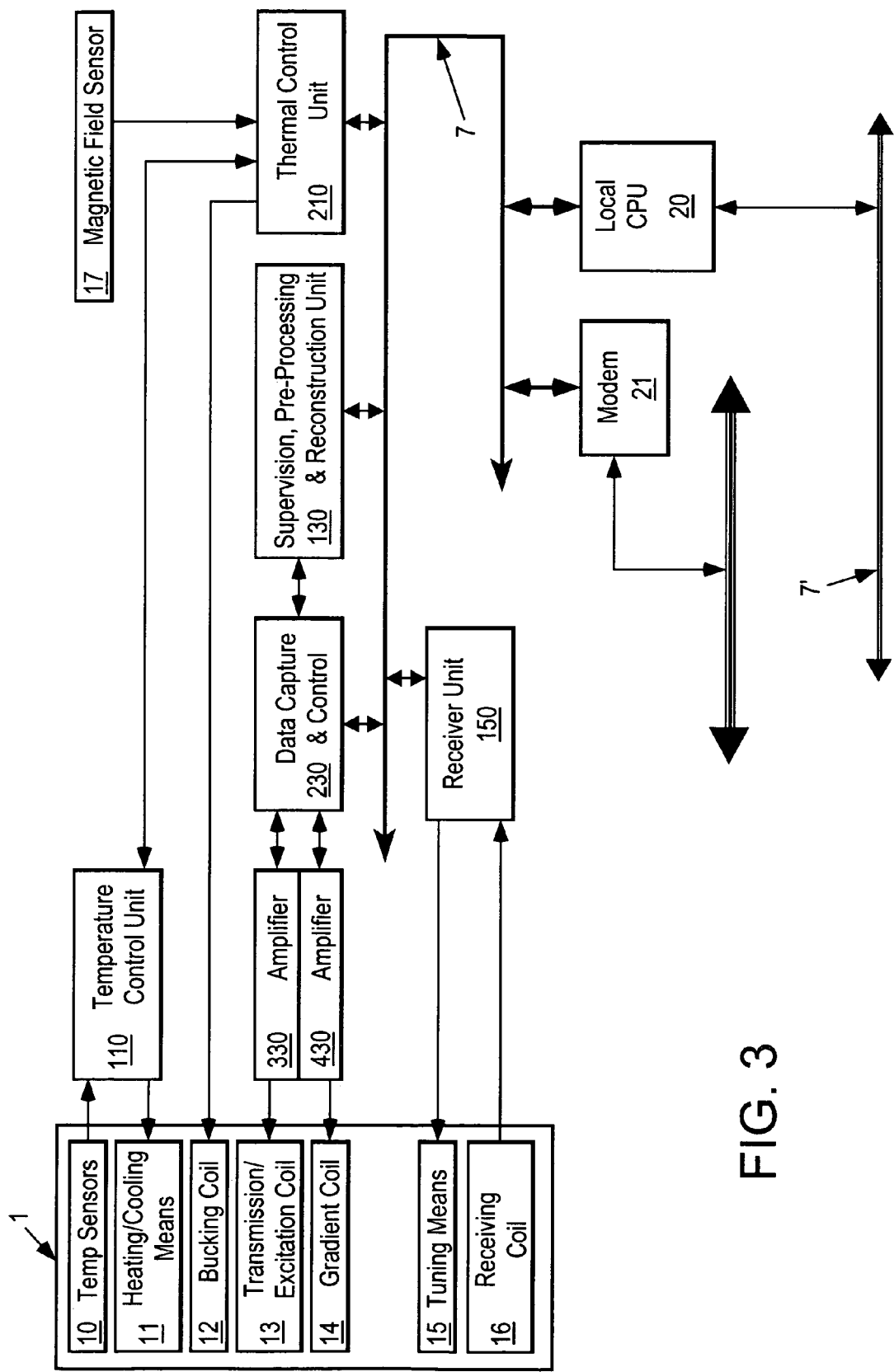
FIG. 3 shows a block diagram of a variant embodiment of the apparatus of FIGS. 1 and 2 in which the client computer system has a different configuration.

A configuration example of a machine according to the invention, fit for this configuration, is shown in FIG. 3. Same functions or means in this figure are denoted with same numerals. As is evident from the comparison with FIG. 2, the units that are expressly dedicated to the control of the magnetic unit and to the reception of echo signals, as well as to signal processing to extract image data are identical to those described with reference to FIG. 2.

However, unlike the previous example, the apparatus has no dedicated peripheral, but includes a local CPU unit which controls the communications between the internal bus 7' and the communication bus, e.g. a LAN network or the like 7, which CPU is denoted with numeral 20 forming a basic minimum configuration of the client computer resident in the frame of the apparatus. A modem 21 may be also provided to allow communication via telephone lines.

The local CPU 20, whereto local memories may be associated, has the only task to access a local server computer via the LAN network, which local server computer integrates the units as described in FIG. 2 and is designed to control several machines. As mentioned above, the local server computer may in turn be a client computer of another server computer for generally controlling several local server computers and therewith several groups of apparatuses which may be used for example in different divisions of an hospital or the like.

The presence of an internal controlling CPU 20 does not cause a real cost increase, both due to the comparatively little cost of CPUs and to the fact that this configuration allows to reduce the number of computers dedicated to the control of machines. In this basic minimum configuration of the client computer the computational power requested is very limited since the local CPU 20 has the only task to control the communications between the specific driver units 210, 230, 130, 150 and the server computer.

Moreover, the local CPU may be used to also control local peripherals, such as storage, display, print and control entry means as it is illustrated and described with reference to FIG. 2.

It shall be noted that the presence of a local CPU 20 does not even hinder the possibly desired provision of one or more apparatuses having a dedicated console.

Referring to the Figures, an additional advantageous characteristic of the invention may be noted. Dedicated apparatuses must be often provided with external supports for limbs or parts of limbs which are not to be received in the cavity or imaging space. For example, if a knee has to be imaged, the other leg of the patient should remain out of the magnetic structure 1. In order to allow the patient to take a comfortable position, the magnetic unit case has side extensions 201 which act as cabinets for housing the units mounted within the case of the magnetic unit and at the same time as supports for the limbs that are not housed in the imaging space. Therefore, the need to create a space for accommodating the electronic units which are permanently associated to the magnetic structure are combined with the needs to create external supports for the magnetic structure itself, wherefore the possible size increase caused by the invention is anyway compensated for by the use thereof as support elements.

The invention is not limited to the configurations of Nuclear Magnetic Resonance imaging apparatuses as shown and illustrated herein, but is also applicable to any type of apparatus, both in the specific field of non invasive imaging, i.e. ultrasound, x-ray imaging, or the like, and in other fields like the detection of physiological or analytical parameters. In this case, the architecture provided by the invention is particularly advantageous because it allows easy data collection and exchange among the different apparatuses, as well as the central control thereof.

Further, with specific reference to Nuclear Magnetic Resonance imaging apparatuses, the invention is not limited to the configurations of the units associated to the magnetic unit as shown and described herein. All the above without departure from the guiding principle disclosed above and claimed below.

The invention claimed is:

1. A nuclear magnetic resonance imaging apparatus network, comprising two or more magnetic resonance imaging apparatuses connected to a same server computer, wherein each of the magnetic resonance imaging apparatuses has an excitation and receiving unit and a driving unit for the excitation and receiving unit and a different client computer,
wherein the network includes a communication bus to which each of the client computers is connected and each of the driving units includes one or more electronic cards, and each of the cards has an input/output interface with the communication bus, while the input data and output data exchanged between the electronic cards is coded according to common data coding protocols.

2. The nuclear magnetic resonance imaging apparatus network according to claim 1, wherein at least part of peripherals of different client computers may be shared by the apparatuses connected to the network.

3. The nuclear magnetic resonance imaging apparatus network according to claim 1, wherein a client/server architecture is applied to at least one of ultrasound and radiographic examination apparatuses connected to the network, the server computer being provided with controlling, processing and displaying programs for each of the at least one examination apparatuses connected to the network.

4. The nuclear magnetic resonance imaging apparatus according to claim 1, wherein the server computer is a regional server which is a client of a central server controlling a network formed by more than one regional server each regional server controlling one or more MRI apparatuses.

5. The nuclear magnetic resonance imaging apparatus according to claim 1, wherein each of the driving units of the exciting and receiving units includes, a central image data supervision, a pre-processing and reconstruction unit which controls a control and capture unit as well as a thermal and magnetic control unit, and a receiver unit which are provided with a communication controller and are connected to one another and to the client computer and its peripherals and through the client computer to the server computer and its peripherals by using the same bus or the same communication lines.

* * * * *